United States Patent
Streicher et al.

(10) Patent No.: US 6,461,482 B1
(45) Date of Patent: Oct. 8, 2002

(54) PROCESS FOR PREPARING HIGH-PURITY PHYTANTRIOL

(75) Inventors: Harald Streicher, Ludwigshafen; Wolfram Burst, Mannheim; Jürgen Däuwel, Lustadt; Jürgen Koppenhöfer, Meckenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/492,067

(22) Filed: Jan. 27, 2000

(30) Foreign Application Priority Data

Jan. 28, 1999 (DE) .......................... 199 03 459

(51) Int. Cl.⁷ .......................... B01D 3/10; C07C 29/80; C07C 31/22
(52) U.S. Cl. .......................... 203/91; 203/86; 203/100; 202/158; 568/867; 568/868
(58) Field of Search .......................... 202/158, 205; 203/100, 91, 86, 1, 2; 261/DIG. 72, 112.2; 568/868, 867; 159/47.1, 43.1

(56) References Cited

U.S. PATENT DOCUMENTS

| | | | | |
|---|---|---|---|---|
| 4,471,014 A | * | 9/1984 | den Hartog et al. | 261/DIG. 72 |
| 4,950,430 A | * | 8/1990 | Chen et al. | 261/112.2 |
| 5,132,056 A | * | 7/1992 | Lockett et al. | 261/112.2 |
| 5,188,773 A | * | 2/1993 | Chen et al. | 261/112.2 |
| 5,777,173 A | * | 7/1998 | Paust et al. | 203/5 |
| 5,950,454 A | * | 9/1999 | Burst et al. | 62/643 |
| 6,111,117 A | * | 8/2000 | Hartmann et al. | 549/413 |

FOREIGN PATENT DOCUMENTS

| | | |
|---|---|---|
| DE | 1 142 428 | 1/1963 |
| DE | 1 149 700 | 6/1963 |
| DE | 27 10 859 | 9/1968 |
| DE | 1 467 925 | 1/1969 |
| DE | 39 12 478 | 10/1990 |
| DE | 42 15 501 | 10/1993 |
| DE | 42 34 744 | 4/1994 |
| DE | 44 07 728 | 3/1995 |
| DE | 195 24 928 | 1/1997 |
| EP | 0 512 277 | 11/1992 |
| EP | 0 679 383 | 11/1995 |
| EP | 0 686 386 | 12/1995 |
| JP | 61-236737 | 10/1986 |
| JP | 4-69316 | 4/1992 |

* cited by examiner

Primary Examiner—Virginia Manoharan
(74) Attorney, Agent, or Firm—Oblon, Spivak, McClelland, Maier & Neustadt, P.C.

(57) ABSTRACT

A process for preparing high-purity phytantriol, that includes rectifying the phytantriol which is obtained and is contaminated with lower and/or higher boiling byproducts under medium vacuum in rectification columns containing metal cloth packings with ordered structure using channel liquid distributors with a minimum of 500 drip points/m², which are arranged at an angle of 90° to the cloth layers of the packing elements located directly below the distributors, in which 2 or more of the packing elements underneath the liquid distributors have only a small height, which ensure absolute exclusion of air and a strictly adiabatic procedure.

The preparation of high-purity phytantriol takes place particularly advantageously when the phytantriol which is contaminated with byproducts is a phytantriol which has been obtained by reacting isophytol with performic acid and subsequently hydrolyzing the product formed in the reaction with alkaline agents in a manner known per se.

7 Claims, 2 Drawing Sheets

PROCESS FOR PREPARING HIGH-PURITY PHYTANTRIOL

The invention relates to a process for the preparation and final purification by distillation of 3,7,11,15-tetramethyl-1,2,3-trihydroxyhexadecane (phytantriol) of

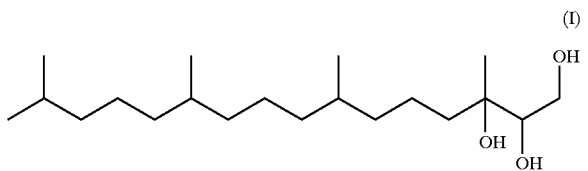

(I)

which is in demand as an addition to skin and hair care compositions.

Phytantriol is in demand in the cosmetics industry as humectant and as penetration enhancer for cosmetic active ingredients such as panthenol, vitamin A and vitamin E (cf., for example, DE 42 15 501, EP 686 386, EP 679 383, DE 42 34 744, JP 04069316, JP 61236737, DE 14 67 925 and DE 11 42 428).

Essentially two industrial processes for preparing this active ingredient are known.

1) DE 1 149 700 discloses a process for preparing trihydric alcohols of the general formula II

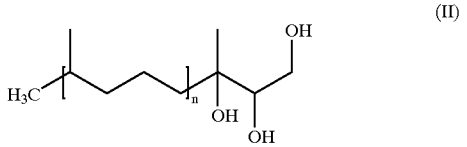

(II)

in which tertiary alcohols of the general formula III

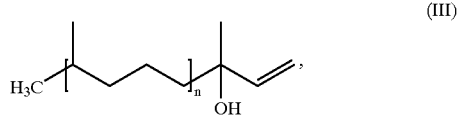

(III)

such as isophytol (n=3) can be reacted in a manner known per se with an organic peracid, in particular with performic acid, followed by alkaline hydrolysis to prepare phytantriol (I).

The disadvantage of this process is that the resulting trihydric alcohols, which easily decompose at high temperatures, are heavily contaminated by byproducts which have approximately equally high boiling points, and therefore cannot be prepared in the purity required for cosmetic purposes even on fractional distillation under high vacuum (about $10^{-1}$ to $10^{-5}$ mbar) such as short-path distillation or molecular distillation. Apart from the fact that such separations under high vacuum entail both very high capital costs and high running costs, only insufficiently pure products can be obtained at justifiable expense from such mixtures with low relative volatilities. High purities are obtained only with extremely complicated apparatus and extremely low distillation yields.

2) Japanese Patent Publication JP 61236737 A2 discloses a process for preparing phytantriol in which the latter is obtained in somewhat greater purity. In this process, isophytol is reacted in the presence of vanadium or molybdenum compounds with tert-butyl hydroperoxide [$(CH_3)_3$C—OOH], and an opening of the epoxide rings in the resulting epoxy compounds is then carried out with acidic catalysts. The crude phytantriol obtained in this way is then purified by molelcular distillation under 0.22 mbar.

The disadvantages of this process are the use of heavy metals, which is undesirable in the cosmetics industry, the relatively elaborate process management and the need to purify by molecular distillation.

It is an object of the present invention to prepare phytantriol, which is in demand as active ingredient in the cosmetics industry, in very pure form on an industrial scale in a simple manner without using heavy metal compounds and without the need to purify under high vacuum.

We have found that this object is achieved by subjecting contaminated phytantriol, in particular the phytantriol which can be prepared in a relatively simple manner by the process of DE 1 149 700 but is contaminated with lower and/or higher boiling colored additional components to a very specific rectification under medium vacuum (i.e. with an overhead vacuum of from 0.1 to 2 mbar) to result in very pure product in a high distillation yield without costly molecular distillation.

Although DE 19524928 discloses a process for obtaining pure substances from mixtures of high boiling air- and/or temperature-sensitive substances requiring high separation efficiency by rectification under specific conditions under medium vacuum, it was nevertheless very surprising that even the high boiling phytantriol, which is extremely sensitive to thermal stresses, can be rectified under medium vacuum with distillation yields of up to 95% of theory to give high-purity phytantriol (purity>99%). This is particularly true since it is evident from the UIC-News of Norbert Kukla UIC GmbH of Dec. 7, 1998 that even one of the significant manufacturers of phytantriol, despite intensive research into the ultrapurification of phytantriol, regards only short-path distillation, i.e. a very complex distillation under extremely high vacuum, as suitable, although the research, as demonstrated by the statements in said UIC-News, had the aim of meeting not only higher quality requirements but also the understandable requirement for increased productivity and reduction of costs.

The invention accordingly relates to a process for preparing high-purity phytantriol, which comprises rectifying phytantriol which is contaminated with lower and/or higher boiling colored byproducts under medium vacuum in columns containing metal packings with ordered structure, wherein a) the liquid distribution is carried out by channel distributors with a minimum of 500 drip points per $m^2$, b) the channels of the liquid distributors are arranged at an angle of about 90° to the cloth layers of the packing elements located directly below these distributors, c) 2 or more packing elements which have a height of only 20 to 100 mm and whose cloth layers are each rotated by 90° relative to one another are inserted underneath the liquid distributors, d) air is absolutely excluded during operation, and e) the rectification is carried out strictly adiabatically.

Figure 1:
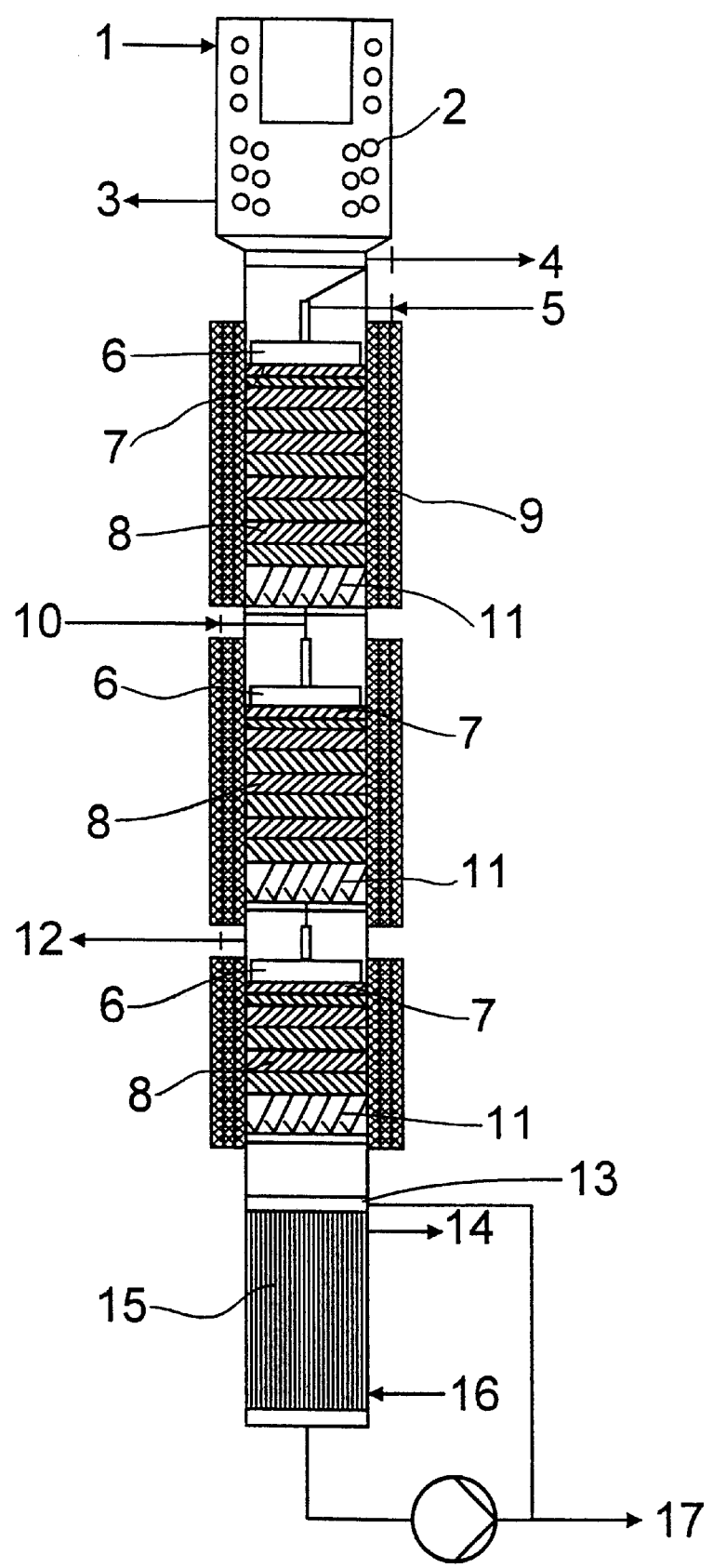
FIG. 1 shows a packed column which can be used for rectification of phytantriol.

The preparation of high-purity phytantriol takes place particularly advantageously when the phytantriol which is contaminated with byproducts is a phytantriol which has been obtained by the process disclosed in DE 1 149 700 by reacting isophytol with performic acid and subsequently hydrolyzing the product formed in the reaction with alkaline agents.

In the reaction of isophytol with performic acid there is presumably, in a first reaction, rearrangement of the isophytol employed as starting compound in an allylic rearrangement to phytyl formate, in which the $\beta,\gamma$ double bond produced in this way is subsequently epoxidized by the action of performic acid. There is finally formation, from the resulting 1-formyloxy-2,3-epoxyphytol, of 1,3-diformyloxy-2-hydroxy-3,7,11,15-tetramethylhexadecane, from which 1,2,3-trihydroxy-3,7,11,15-tetramethylhexadecane is formed by alkaline hydrolysis. It is particularly expedient in this case to carry out the allylic rearrangement completely to form the phytyl formate before the epoxidation is carried out with performic acid. This can advantageously take place by firstly reacting the isophytol with formic acid alone and, only after the allylic rearrangement is complete, allowing the epoxidation to take place by adding hydrogen peroxide, which forms performic acid in situ with the formic acid.

The reaction with performic acid, or with formic acid and hydrogen peroxide, generally takes place at room temperature or slightly elevated temperature, so that temperatures which may be mentioned for the reaction are from 20 to 60° C., preferably 30 to 50° C.

The hydrolysis of the trihydroxy diformate compound to phytantriol takes place with alkaline agents. It would be possible to use for this purpose, for example, dilute sodium hydroxide solution or potassium hydroxide solution.

The crude phytantriol is obtained as a viscous oil which can be obtained in very pure form (in purities greater than 99%) according to the invention by rectification under medium vacuum.

Generally used for fractionating high boiling mixtures of substances which require a high separation efficiency, i.e. their boiling points are close together, are rectification columns having packings systematically built up in regular geometry and having defined passage regions for the countercurrent phases, because regularly structured packings are distinguished from random packings by the possibility of greater loading and a better separating effect, and have a lower specific pressure drop, and a smaller necessary packing volume and therefore also a smaller necessary mass and heat transfer height. They are therefore employed in all vacuum rectifications in which, owing to the temperature sensitivity of the mixture to be separated, it is particularly important to limit the pressure drop in the columns. Particularly suitable column packings are metal cloth packings of the BX and CY types supplied by Sulzer (cf. Sulzer company publication "Trennkolonnen fur Destillation und Absorption") and metal cloth packings acting similarly from other suppliers such as Montz GmbH.

A diagrammatic representation of such columns is to be found, for example, on page 103 of the textbook "Thermische Trennverfahren" by Klaus Sattler, VCH Verlagsges.mbH, Weinheim (FRG), 1988. For further details of the rectification of substance mixtures, we refer to this textbook by Klaus Sattler, pages 101–225, in particular 120–160 and 199–214.

With operating columns, overhead pressures of 0.5 mbar can thus be achieved with acceptable technical complexity. The highest product temperature occurs in the bottom of a column. It is determined not only by the overhead pressure but also by the pressure drop of the column internals which is related to the separation efficiency required.

The thermal stressability of many high boiling mixtures is so low that, despite the use of the described metal cloth packings with ordered structure and overhead pressures in the column of only 0.5 to 1 mbar, the temperatures which would occur in the bottom due to the pressure drop on the cloth packings required for the necessary separation efficiency are above the decomposition range of the compounds to be separated. Thus, for the fractional distillation of such mixtures to date the high vacuum range (about $10^{-1}$ to $10^{-5}$ mbar) has generally been used, i.e. either short-path distillation or molecular distillation have been used. However, for mixtures with low relative volatilities, high purities can be obtained in these distillations only with low distillation yields.

With operating columns, overhead pressures of from 0.5 to 1 mbar can be achieved with acceptable technical complexity. The boiling point of phytantriol under a pressure of 1 mbar is about 200° C. The limited thermal stability of phytantriol is the reason that the temperature in the bottom of the column is limited to about 210 to 230° C. A rectification column may therefore be operated with a maximum bottom pressure of only 3 mbar. This means that only a pressure drop of about 2 to 2.5 mbar between the top and bottom of the column can be tolerated. This is very difficult to achieve because a separation efficiency of about 10 to 30 separation stages is necessary for final purification of phytantriol, and a pressure drop of from 0.3 to 0.5 mbar must usually be expected for each separation stage.

Feature a) of the main claim specifies a liquid distribution with channel distributors with a minimum of 500 drip points. Similar distributors, which are also called "capillary distributors" but are round, are marketed by the companies Sulzer and Montz and are described, for example, in EP 512 277. Known channel distributors generally have only 50 to 60 drip points per $m^2$.

The use of channel distributors reduces the pressure drop during the rectification of phytantriol in 2 different ways. This results, on the one hand, in a rapid and extremely fine distribution and thus eventually in better utilization of the packing for distribution of the mixture to be separated and, on the other hand, in a very low trickling density. The lower limit of the liquid flow rates stated for Sulzer packings of the BX type is about 0.2 $m^3/m^2 \cdot h$. Through the use, according to the invention, of the channel distributors with a minimum of 500, preferably 900 to 1200, drip points the liquid flow rates achieved with phytantriol in the process according to the invention are only 0.03 to 0.3 $m^3/m^2 \cdot h$ at the top and 0.03 to 1.0 $m^3/m^2 \cdot h$ in the stripping section of the column. It has been found, surprisingly, that even with such low liquid flow rates the complete wetting of the metal packings, which is required for optimal separation efficiency, is ensured. This low trickling density means that the gas flow rate in the column and thus the pressure drop is extremely low.

However, to obtain an optimal separation efficiency it is important not only to have a large number of drip points but also to arrange the distributors having regard to the packing elements.

One layer of a cloth packing generally consists of a multiplicity of, usually single, cloth layers which are 170 mm high. Each packing layer is, when fitted, rotated by in each case 90° in relation to the previous layer. The distributors are likewise arranged rotated by 90° in relation to the packing element located directly below the distributors.

The liquid then spreads out on one of these cloth layers at a particular angle. After an inflow length which depends on the spreading angle and the distance between two drip points, a uniform film has formed over a cloth layer.

Optimal utilization of the packing, i.e. the fastest possible distribution of the liquid on all cloth layers, is achieved when the packing is rotated by 90° at this point.

Thus, in the purification process according to the invention, 2 or more packing elements which have a height of only 20 to 100 mm, preferably 25 to 50 mm, in particular 35 to 45 mm, and whose cloth layers are each rotated by 90° relative to one another are inserted underneath the liquid distributors. The separation of the packing into elements of smaller height means that the fastest possible distribution and thus optimal utilization of the packing for the separation can be achieved. By contrast, in the conventional arrangement of packing, the inflow length is about 340 mm, which means that with a packing height of 2 meters about 17% of the packing is not fully utilized for the actual separation operation.

According to feature d), the rectification is to be carried out with absolute exclusion of air.

Laboratory tests have shown that in the case of phytantriol at the high temperatures required for the rectification even the slightest leaks in the distillation equipment result in the product darkening in color, which cannot be tolerated because of the high quality requirements. The use of newly developed, particularly high-quality sealing materials such as Helicoflex® supplied by Cefilac for sealing flanges and/or openings for devices to monitor the process is therefore absolutely necessary. It is particularly advantageous to seal flanges by using welded lip seals as described, for example, in German Patents DE 27 10 859, DE 39 12 478 or DD 44 07 728.

As already explained, only small mass flows circulate in the medium vacuum rectification columns according to the invention. Thus every loss of heat immediately leads to uncontrolled condensation on the column wall, which reduces the separation efficiency of the column. Strictly adiabatic operation of the column can best be ensured by a combination of insulation and protective heating of the column.

Such protective heating is advantageously achieved industrially in the following way: A metal plate jacket is attached to a first insulating layer on the column jacket so that this metal plate jacket is insulated again. Another metal plate jacket and the heating are then attached to this insulating layer, and the heating is finally insulated toward the outside. The heating is then controlled in such a way that the temperature difference between the column jacket and the first metal plate jacket is zero.

For the final purification of phytantriol according to the invention it is necessary to operate the rectification with overhead pressures of from 0.2 to 1 mbar, preferably 0.5 to 1 mbar, and with bottom pressures of from 1 to 4 mbar, preferably 1.5 to 3.5 mbar, in particular 2 to 3 mbar.

Because of the thermal instability, the rectification of phytantriol can be carried out in accordance with the main claim, i.e. with use of the known cloth packings in pack columns with a maximum height of 5 m.

In the rectification of phytantriol according to the invention, the packed columns are operated with a liquid flow rate between 0.03 and 0.3 m$^3$/m$^2$·h in the concentrating section of the column and with a liquid flow rate between 0.03 and 1.0 m$^3$/m$^2$·h in the stripping section of the columns.

A packed column which can be employed for the rectification of phytantriol is depicted diagrammatically in FIG. 1.

The meanings in this are:
1 Inlet for cooling medium
2 Condenser
3 Outlet for cooling medium
4 Distillate
5 Reflux
6 Channel liquid distributors with a minimum of 500 drip points/m$^2$
7 Packing elements with a height of from 20 to 100 mm
8 Packing elements with a height of about 170 mm
9 Protective heating
10 Inlet for crude phytantriol
11 Liquid collectors
12 Side discharge
13 Sealing element
14 Outlet for heating medium (exit)
15 Falling film evaporator
16 Inlet for heating medium (entry)
17 Bottom discharge.

Figure 2A:
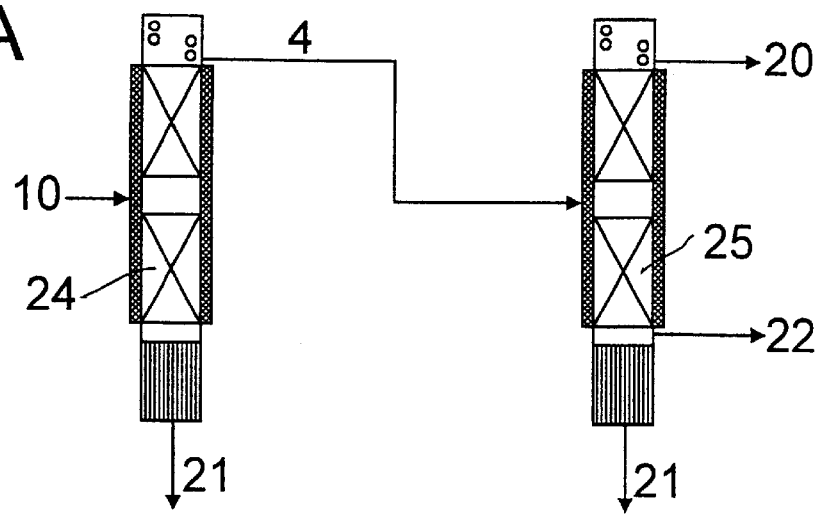
FIG. 2a and 2b depict two possible distillation concepts for the rectification of phytantriol in two packed columns.
Figure 2B:
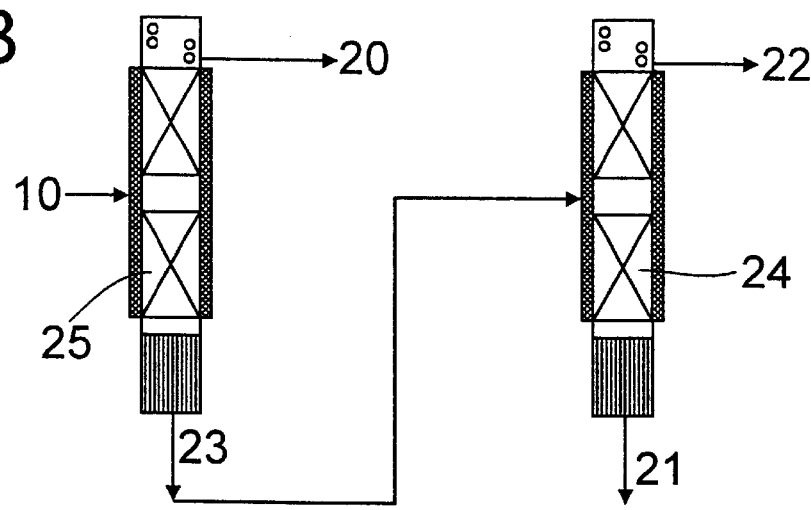

To remove colored lower boiling impurities and colored higher boiling impurities, 2 columns are necessary in general and in the case of phytantriol. FIGS. 2a and 2b depict diagrammatically 2 possible distillation concepts for the rectification of phytantriol in 2 packed columns. The meanings in these are:
10 Inlet for phytantriol
20 Outlet for low boilers
21 Outlet for high boilers
4 Distillate
22 Outlet for pure phytantriol, i.e. purity>99%
23 Bottom stream
24 Rectification to remove high boilers
25 Rectification to remove low boilers However, it is also possible to use only one column in two consecutive steps, or else to use distillation equipment which is equivalent to the use of two columns, such as a so-called baffle plate column. A baffle plate column is, in general, a combination of 2 separate column packings within an outer column jacket on which inlet and side discharge are located.

Figure 2C:
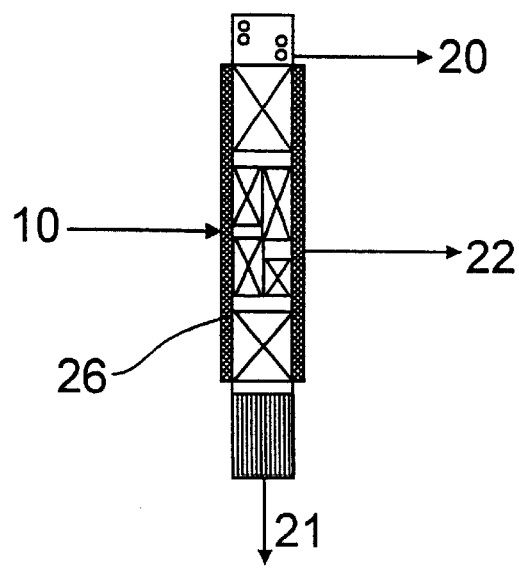
FIG. 2c depicts a baffle plate columns.

Such a baffle plate column is depicted diagrammatically in FIG. 2c. In this, 10, 20, 21 and 22 have the same meanings as in FIGS. 2a and 2b and 26 means a baffle plate columnn.

The rectification process according to the invention makes it possible to rectify impure phytantriol, in particular the impure phytantriol obtained on reaction of isophytol with performic acid and subsequent alkaline hydrolysis, also under medium vacuum, i.e. under pressures of from 0.2 to 2 mbar, preferably 0.5 to 1 mbar, in columns with cloth packings with a low pressure drop, and with distillation yields of up to 95%.

Description by way of example of the process for purifying phytantriol with columns shown in FIG. 1 by the distillation concept shown in FIG. 2a.

The phytantriol prepared by the process described in DE 1 149 700 with a content of about 85% was introduced at a temperature between 150 and 200° C. through the inlet 10 into the middle of the first rectification column containing a height of from 3 to 5 m of packings of the Sulzer BX or Montz A3 type. The liquid was distributed uniformly over the cross section of the column at the top and at the inlet to the column by the newly developed high-efficiency channel distributors 6. The packing elements 7 with a height of only 20 to 100 mm were located underneath the channel distributors. The cloth layers of the packing elements arranged directly below the channel distributors 6 were rotated by an angle of 90° with respect to the channels of the liquid distributors. The column was equipped with a protective heating 9 and was operated adiabatically. Flanges and connections were provided with welded lip seals or high-quality metal seals.

The overhead pressure in the first column was about 0.5 to 1 mbar. The reflux ratio was 0.5 to 2. The liquid flowing back in the column had a temperature between 130 and 180° C. 5 to 20% of the inlet stream were removed at the bottom of the column.

The product removed at the top of the first column at a temperature of 150 to 200° C. was delivered into the middle of the second rectification column with a height of 3 to 5 m of packings of the Sulzer BX or Montz A3 type. The liquid was distributed over the column cross section at the top and at the inlet by the newly developed high-efficiency channel distributors. This column was also equipped with a protective heating and was operated adiabatically. Flanges and connections were provided with welded lip seals or high-quality metal seals.

The overhead pressure of the second column was about 0.5 mbar. The reflux ratio was 2 to 5. The liquid flowing back into the column had a temperature between 130 and 180° C. 5 to 20% of the inlet stream were removed at the top and bottom of the column. The phytantriol removed in the side discharge directly above the vaporizer in the second column was virtually colorless (APHA color number less than 10) and had a purity of more than 99%. The yield of product of this purity was up to 95% of theory.

We claim:

1. A process for preparing purified phytantriol, consisting of:

rectifying phytantriol which is contaminated with lower and/or higher boiling byproducts under medium vacuum in columns containing metal cloth packings with ordered structure, and carrying out the rectification in a mass transfer column, wherein
   a) liquid distribution is carried out by channel distributors with a minimum of 500 drip points per $m^2$,
   b) the channels of the liquid distributors are arranged at an angle of about 90° to the cloth layers of the packing elements located directly below these distributors,
   c) 2 or more packing elements which have a height of 20 to 100 mm and whose cloth layers are each rotated by 90° relative to one another are located below the liquid distributors,
   d) air is virtually excluded during operation, and
   e) the rectification is carried out adiabatically.

2. A process as claimed in claim 1, wherein the phytantriol that is contaminated with lower and/or higher boiling byproducts is a phytantriol which has been obtained by reacting isophytol with performic acid and subsequently hydrolyzing the product formed in the reaction with alkaline agents.

3. A process as claimed in claim 1, wherein the liquid distribution in a) is carried out with channel distributors with 900 to 1200 drip points per $m^2$.

4. A process as claimed in claim 1, wherein the virtual exclusion of air in d) is ensured by using welded lip seals.

5. A process as claimed in claim 1, wherein the adiabatic operation of the column in e) is ensured by a combination of insulation and protective heating of the column.

6. A process as claimed in claim 1, wherein overhead pressures of from 0.5 to 1 mbar and bottom pressures of from 1 to 4 mbar are used in the rectification of phytantriol.

7. A process as claimed in claim 1, wherein the columns are operated with a liquid flow rate between 0.03 and 0.3 $m^3/m^2 \cdot h$ at the top and a liquid flow rate between 0.03 and 1.0 $m^3/m^2 \cdot h$ in the stripping section during the rectification of phytantriol.

\* \* \* \* \*